United States Patent
Feain et al.

(10) Patent No.: US 11,040,220 B2
(45) Date of Patent: Jun. 22, 2021

(54) METHOD AND SYSTEM FOR IN SITU TARGETING OF OBJECTS

(71) Applicant: ASTO CT, INC, Madison, WI (US)

(72) Inventors: Ilana Feain, Maroubra (AU);
Chun-Chien Shieh, Arncliffe (AU);
Paul Keall, Greenwich (AU)

(73) Assignee: ASTO CT, INC, Middleton, WI (US)

( * ) Notice: Subject to any disclaimer, the term of this patent is extended or adjusted under 35 U.S.C. 154(b) by 108 days.

(21) Appl. No.: 15/557,330

(22) PCT Filed: Mar. 11, 2016

(86) PCT No.: PCT/AU2016/000086
§ 371 (c)(1),
(2) Date: Sep. 11, 2017

(87) PCT Pub. No.: WO2016/141416
PCT Pub. Date: Sep. 15, 2016

(65) Prior Publication Data
US 2018/0050222 A1 Feb. 22, 2018

(30) Foreign Application Priority Data

Mar. 12, 2015 (AU) .............................. 2015900886

(51) Int. Cl.
*A61N 5/10* (2006.01)
*A61B 6/03* (2006.01)
(Continued)

(52) U.S. Cl.
CPC ............ *A61N 5/1049* (2013.01); *A61B 6/032* (2013.01); *A61B 6/4085* (2013.01); *A61B 6/486* (2013.01);
(Continued)

(58) Field of Classification Search
CPC ......... G06T 7/0012; G06T 2207/30096; G06T 7/11; G06T 2207/10081;
(Continued)

(56) References Cited

U.S. PATENT DOCUMENTS 7,894,649 B2 * 2/2011 Fu ........................ A61N 5/1049
382/128
7,894,664 B2 * 2/2011 Kerwin .................... G06K 9/00
382/155
(Continued)

FOREIGN PATENT DOCUMENTS

CN 101076282 11/2007
WO WO 2018090091 A1 5/2018

OTHER PUBLICATIONS

Kirschner, The Probabilistic Active Shape Model: From Model Construction to Flexible Medical Image Segmentation, Jul. 18, 2013 [ retrieved Sep. 22, 2019], Technische Universitat, Darmstadt, Ph.D. Thesis, 209 pages total. Retrieved: https://tuprints.ulb.tu-darmstadt.de/3519/ (Year: 2013).*
(Continued)

*Primary Examiner* — Andrew M Moyer
*Assistant Examiner* — Dennis Rosario
(74) *Attorney, Agent, or Firm* — Casimir Jones S.C.; Thomas Isenbarger (57) ABSTRACT

A method for tracking a target located within a body, whilst scanning the body using X-ray projections, the method including the steps of: (a) providing a first prior image of the body and target indicating their relative position; (b) iteratively performing, for a series of time intervals, the steps of: (i) acquiring a few spatially distributed x-ray projections of the target area; (ii) determining one of a series of motion phases for each x-ray projection; (iii) performing an iterative reconstruction of the image for each of the motion phases;
(Continued)

and (iv) outputting a resultant image for a current time interval.

7 Claims, 6 Drawing Sheets

(51) Int. Cl.
  G01N 23/046 (2018.01)
  A61B 6/00 (2006.01)
  G06T 11/00 (2006.01)
  G06T 7/70 (2017.01)
  G06T 7/00 (2017.01)
  A61B 5/113 (2006.01)

(52) U.S. Cl.
  CPC ............... *A61B 6/487* (2013.01); *A61B 6/50* (2013.01); *A61B 6/5205* (2013.01); *A61B 6/5288* (2013.01); *A61N 5/1031* (2013.01); *A61N 5/1037* (2013.01); *A61N 5/1039* (2013.01); *G01N 23/046* (2013.01); *G06T 7/0012* (2013.01); *G06T 7/70* (2017.01); *G06T 11/003* (2013.01); *G06T 11/006* (2013.01); *A61B 5/113* (2013.01); *A61N 2005/1061* (2013.01); *G01N 2223/401* (2013.01); *G01N 2223/419* (2013.01); *G06T 2207/10081* (2013.01); *G06T 2211/412* (2013.01); *G06T 2211/424* (2013.01); *G06T 2211/428* (2013.01)

(58) Field of Classification Search
  CPC . G06T 2207/30004; G06T 2207/30061; G06T 2207/30064; G06T 2207/20116; G06T 7/0016; G06T 2207/10072; G06T 2207/20152; G06T 2207/20168; G06T 7/12; G06T 7/136; G06T 7/143; G06T 7/149; G06T 7/155; G06T 2207/10088; G06T 2207/10116; G06T 2207/30024; G06T 2210/41; G06T 7/0014; G06T 7/20; G06T 2207/10076; G06T 7/251; G06T 2211/412; G06T 11/005; A61B 6/032; A61B 5/055; A61B 34/10; A61B 6/025; A61B 6/4085; A61B 6/488; A61B 2034/2065; A61B 6/5288; A61B 6/541; A61B 5/7285; A61B 5/7289; A61B 5/113; A61B 5/1128; A61B 6/486; A61B 6/5264; G06K 2209/05; G06K 9/46; G06K 9/0014; G06K 2209/051; G06K 2209/053; G06K 9/3233; G06K 2209/057; A61N 5/1049; A61N 5/1037; A61N 2005/1061; A61N 5/1039; A61N 2005/1054; A61N 5/1067; A61N 2005/1062; A61N 2005/1058; A61N 2005/1055; G01R 33/56509
  See application file for complete search history.

(56) References Cited

U.S. PATENT DOCUMENTS

| | | | | |
|---|---|---|---|---|
| 8,239,005 | B2* | 8/2012 | Wright | A61B 34/20 600/427 |
| 8,363,953 | B2* | 1/2013 | Kameyama | H04N 19/46 382/195 |
| 8,460,166 | B2* | 6/2013 | Guckenburger | A61N 5/103 600/1 |
| 8,824,762 | B2* | 9/2014 | Rivaz | A61B 8/485 382/131 |
| 9,105,095 | B2* | 8/2015 | Maizeroi-Eugene | G06T 17/10 |
| 2009/0161933 | A1 | 6/2009 | Chen | |
| 2014/0050297 | A1 | 2/2014 | Mostafavi | |
| 2015/0279031 | A1 | 10/2015 | Cavusoglu et al. | |
| 2015/0314138 | A1 | 11/2015 | Maurer et al. | |

OTHER PUBLICATIONS

Lu et al., An integrated approach to segmentation and nonrigid registration for application in image-guided pelvic radiotherapy, Oct. 2011 [retrieved Sep. 23, 2019], Medical Image Analysis, vol. 15, Issue 5, pp. 772-785. Retrieved: https://www.sciencedirect.com/science/article/pii/S1361841511000624 (Year: 2011).*

Cootes et al, The use of active shape models for locating structures in medical images, 1993 [retrieved Sep. 22, 2019], Information Processing in Medical Imaging. IPMI 1993:Lecture Notes in Computer Science, vol. 687,pp. 33-47, Retrieved: https://rd.springer.com/chapter/10.1007/BFb0013779 (Year: 1993).*

Hugo, Marker-free lung tumor trajectory estimation from a cone beam CT sinogram, Apr. 14, 2010 [retrieved Apr. 25, 2020], Physics in Medicine & Biology, vol. 55, No. 9, 15 pages. Retrieved: https://iopscience.iop.org/article/10.1088/0031-9155/55/9/014/meta (Year: 2010).*

Shieh et al., Improving thoracic four-dimensional conebeam CT reconstruction with anatomicaladaptive image regularization (AAIR), Jan. 7, 2015 [retrieved Sep. 12, 2020], Physics in Medicine & Biology,vol. 60, p. 841. Retrieved: https://iopscience.iop.org/article/10.1088/0031-9155/60/2/841/meta (Year: 2015).*

Yang et al., A Novel Markerless Technique to Evaluate Daily Lung Tumor Motion Based on Conventional Cone-Beam CT Projection Data, Apr. 2012 [retr Sep. 11, 2020], Inter Jour Radia Oncology*Biology*Physics, vol. 82, Iss 5,p. e749-e756. https://doi.org/10.1016/j.ijrobp.2011.11.035 (Year: 2012).*

Zacharaki et al., ORBIT: A Multiresolution Framework for Deformable Registration of Brain Tumor Images, Aug. 2008 [retrieved Sep. 11, 2020], IEEE Transactions on Medical Imaging, vol. 27, No. 8, pp. 1003-1017. Retrieved: https://ieeexplore.IEEE.org/abstract/document/4436040 (Year: 2008).*

Fletcher-Heath et al., Automatic segmentation of non-enhancing brain tumors in magnetic resonance images, Jan.-Mar. 2001 [ retrieved Sep. 11, 2020], Artificial Intelligence in Medicine, vol. 21, Iss:1-3,pp. 43-63. Retrieved: https://www.sciencedirect.com/science/article/pii/S0933365700000737 (Year: 2001).*

Lung Cancer Radiotherapy Using Realtime Dynamic Multileaf Collimator (MLC) Adaptation and Radiofrequency Tracking (LIGHTSABR) [webpage], last updated: Sep. 11, 2019 [retrieved: Mar. 19, 2021], Retrived: https://clinicaltrials.gov/ct2/show/study/NCT02514512?term=02514512&recrs=ab&draw=2&rank=1 (Year: 2019).*

International Search Report for Application No. PCT/AU2016/000086 dated May 16, 2016.

Chen, Guang-Hong, Jie Tang, and Shuai Leng. "Prior image constrained compressed sensing (PICCS): A method to accurately reconstruct dynamic CT images from highly undersampled projection data sets." Medical Physics 35.2 (2008): pp. 660-661.

Barnes et al., Dosimetric evaluation of lung tumor immobilization using breath hold at deep inspiration. Int J Radiat Oncol Biol Phys. 2001.

Bryant et al., Registration of clinical volumes to beams-eye-view images for real-time tracking. Med Phys. Dec. 2014;41(12):121703.

Depuydt et al., Treating patients with real-time tumor tracking using the Vero gimbaled linac system: implementation and first review. Radiother Oncol. Sep. 2014;112(3):343-51.

Descovich et al., Characteristics of megavoltage cone-beam digital tomosynthesis. Med Phys. Apr. 2008;35(4):1310-6.

Dobbins III et al., Digital x-ray tomosynthesis: current state of the art and clinical potential. Phys Med Bioi. Sep. 2003; 48(19) R65.

Furtado et al., Real-time 2D/3D registration using kV-MV image pairs for tumor motion tracking in image guided radiotherapy. Acta Oncol. Oct. 2013;52(7):1464-71.

Gendrin et al., Monitoring tumor motion by real time 2D/3D registration during radiotherapy. Radiother Oncol. Feb. 2012;102(2):274-80.

(56) References Cited

OTHER PUBLICATIONS

George et al., On the accuracy of a moving average algorithm for target tracking during radiation therapy treatment delivery. Med Phys. Jun. 2008;35(6):2356-65.

Godfrey et al, Digital tomosynthesis with an on-board kilovoltage imaging device. Int J Radiat Oncol Biol Phys. May 1, 2006;65(1):8-15.

Guckenberger et al., Intra-fractional uncertainties in cone-beam CT based image-guided radiotherapy (IGRT) of pulmonary tumors. Radiother Oncol. Apr. 2007;83(1):57-64.

Hardcastle et al., (2016). MO-FG-BRA-06: Electromagnetic Beacon Insertion in Lung Cancer Patients and Resultant Surrogacy Errors for Dynamic MLC Tumour Tracking. Med. Phys., 43: 3710-3711.

Hong et al., Migration of implanted markers for image-guided lung tumor stereotactic ablative radiotherapy. J Appl Clin Med Phys. Mar. 4, 2013;14(2):4046.

IEC 61217: Radiotherapy Equipment-Coordinates, Movements and Scales 2011 Technical Report International Electrotechnical Commission (TOC only).

Imura et al., Insertion and fixation of fiducial markers for setup and tracking of lung tumors in radiotherapy. Int J Radiat Oncol Biol Phys. Dec. 1, 2005;63(5):1442-7.

International Search Report and Written Opinion Issued in Application No. PCT/AU2017/051261 dated Feb. 27, 2018, 10 pages.

Johnson et al., The ITK Software Guide: Design and Functionality, 4th edn, Kitware Inc., 2015.

Kavanagh et al., Obtaining breathing patterns from any sequential thoracic x-ray image set. Phys Med Biol. Aug. 21, 2009;54(16):4879-88.

Keall et al., The management of respiratory motion in radiation oncology report of AAPM Task Group 76. Med Phys. Oct. 2006;33(10):3874-900.

Kothary et al., Safety and efficacy of percutaneous fiducial marker implantation for image-guided radiation therapy. J Vasc Intery Radiol. Feb. 2009;20(2):235-9.

Kupelian et al., Multi-institutional clinical experience with the Calypso System in localization and continuous, real-time monitoring of the prostate gland during external radiotherapy, 2007 Int. J. Radiat. Oncol. 67 1088-98.

Lewis et al., Markerless lung tumor tracking and trajectory reconstruction using rotational cone-beam projections: a feasibility study. Phys Med Biol. May 7, 2010;55(9):2505-22.

Low et al, A novel CT acquisition and analysis technique for breathing motion modeling. Phys Med Biol. Jun. 7, 2013;58(11):L31-6.

Mattes et al., Nonrigid multimodality image registration, Proc. SPIE 4322, Medical Imaging 2001.

Maurer et al., On-board four-dimensional digital tomosynthesis: first experimental results. Med Phys. Aug. 2008;35(8):3574-83.

Poulsen et al., A method to estimate mean position, motion magnitude, motion correlation, and trajectory of a tumor from cone-beam CT projections for image-guided radiotherapy. Int J Radiat Oncol Biol Phys. Dec. 1, 2008;72(5):1587-96.

Poulsen et al., A method for robust segmentation of arbitrarily shaped radiopaque structures in cone-beam CT projections. Med Phys. Apr. 2011;38(4):2151-6.

Ren et al., A novel digital tomosynthesis (DTS) reconstruction method using a deformation field map. Med Phys. Jul. 2008;35(7):3110-5.

Ren et al., A limited-angle intrafraction verification (LIVE) system for radiation therapy. Med Phys. Feb. 2014;41(2):020701-01-020701-09.

Richter et al., Feasibility study for markerless tracking of lung tumors in stereotactic body radiotherapy. Int J Radiat Oncol Biol Phys. Oct. 1, 2010;78(2):618-27.

Rit et al., The Reconstruction Toolkit (RTK), an open-source cone-beam CT reconstruction toolkit based on the Insight Toolkit (ITK) J. Phys.: Conf. Ser. 489(1), 012079-012079 2014.

Roman et al., Interfractional Positional Variability of Fiducial Markers and Primary Tumors in Locally Advanced Non-Small-Cell Lung Cancer During Audiovisual Biofeedback Radiotherapy, 2012 Int. J. Radiat. Oncol. 83(5)1566-72.

Rottmann et al., Markerless EPID image guided dynamic multi-leaf collimator tracking for lung tumors. Phys Med Biol. Jun. 21, 2013;58(12):4195-204.

Ruan, et al. Real-time profiling of respiratory motion: baseline drift, frequency variation and fundamental pattern change. Phys Med Biol. Aug. 7, 2009;54(15):4777-92.

Santoro et al., Evaluation of respiration-correlated digital tomosynthesis in lung. Med Phys. Mar. 2010;37(3):1237-45.

Seco et al., Dosimetric impact of motion in free-breathing and gated lung radiotherapy: a 4D Monte Carlo study of intrafraction and interfraction effects. Med Phys. Jan. 2008;35(1):356-66.

Schmidt et al., Clinical use of iterative 4D-cone beam computed tomography reconstructions to investigate respiratory tumor motion in lung cancer patients, (2014) Acta Oncologica, 53:8, 1107-1113.

Seiler et al., A novel tracking technique for the continuous precise measurement of tumour positions in conformal radiotherapy. Phys Med Biol. Sep. 2000;45(9):N103-10.

Serpa et al., Suitability of markerless EPID tracking for tumor position verification in gated radiotherapy. Med Phys. Mar. 2014;41(3):031702-01-031702-13.

Shah et al., Intrafraction variation of mean tumor position during image-guided hypofractionated stereotactic body radiotherapy for lung cancer. Int J Radiat Oncol Biol Phys. Apr. 1, 2012;82(5):1636-41.

Sharp et al., Tracking errors in a prototype real-time tumour tracking system. Phys Med Biol. Dec. 7, 2004;49(23):5347-56.

Shieh et al., Markerless tumor tracking using short kilovoltage imaging arcs for lung image-guided radiotherapy. Phys Med Biol. Dec. 21, 2015;60(24):9437-54.

Sonke et al., Frameless stereotactic body radiotherapy for lung cancer using four-dimensional cone beam CT guidance. Int J Radiat Oncol Biol Phys. Jun. 1, 2009;74(2):567-74.

Stevens et al., Respiratory-driven lung tumor motion is independent of tumor size, tumor location, and pulmonary function. Int J Radiat Oncol Biol Phys. Sep. 1, 2001;51(1):62-8.

Tang et al. Fluoroscopic tracking of multiple implanted fiducial markers using multiple object tracking. Phys Med Biol. Jul. 21, 2007;52(14):4081-98.

Teske et al., Real-time markerless lung tumor tracking in fluoroscopic video: Handling overlapping of projected structures. Med Phys. May 2015;42(5):2540-9.

Trofimov et al., Tumor trailing strategy for intensity-modulated radiation therapy of moving targets. Med Phys. May 2008;35(5):1718-33.

Van Der Reijden et al., Motion compensated digital tomosynthesis. Radiother Oncol. Dec. 2013;109(3):398-403.

Van Der Voort et al., Stability of markers used for real-time tumor tracking after percutaneous intrapulmonary placement. International Journal of Radiation Oncology, Biology, Physics. Nov. 2011;81(3):e75-81.

Van Sornsen De Koste et al., Digital tomosynthesis (DTS) for verification of target position in early stage lung cancer patients. Med Phys. Sep. 2013;40(9):091904.

Van Sornsen De Koste et al., Markerless tracking of small lung tumors for stereotactic radiotherapy. Med Phys. Apr. 2015;42(4):1640-52.

Willoughby et al., Target localization and real-time tracking using the Calypso 4D localization system in patients with localized prostate cancer. Int J Radiat Oncol Biol Phys. Jun. 1, 2006;65(2):528-34.

Zhang et al., A technique for estimating 4D-CBCT using prior knowledge and limited-angle projections. Med. Phys. Dec. 2013;40(12):121701-01-121701-16.

AU Examination Report for corresponding App No. 2016228944, dated Oct. 29, 2019, 5 pages.

EP Search Report for corresponding App. No. 16760919.7, dated Apr. 8, 2020,5 pages.

(56) References Cited

OTHER PUBLICATIONS

Office Action issued for corresponding CN Application No. 201680015346.6, dated Feb. 25, 2021, 11 pages.

* cited by examiner

Present approach
FIG. 7

Single kV X-Ray projection
FIG. 6

METHOD AND SYSTEM FOR IN SITU TARGETING OF OBJECTS

RELATED APPLICATIONS

The present invention is a U.S. National Stage under 35 USC 371 patent application, claiming priority to Serial No. PCT/AU2016/000086, filed on 11 Mar. 2016; which claims priority of AU 2015900886, filed on 12 Mar. 2015, the entirety of both of which are incorporated herein by reference.

FIELD OF THE INVENTION

The present invention relates to the field of real time image guided radiotherapy utilised in the treatment of cancers or the like.

REFERENCES

Barnes E, Murray B, Robinson D, Underwood L, Hanson J and Roa W 2001 Dosimetric evaluation of lung tumor immobilization using breath hold at deep inspiration Int. J. Radiat. Oncol. 50 1091-8.

Bryant J H, Rottmann J, Lewis J H, Mishra P, Keall P J and Berbeco R I 2014 Registration of clinical volumes to beams-eye-view images for real-time tracking Med. Phys. 41 121703.

Chen G H, Tang J and Leng S 2008 Prior image constrained compressed sensing (PICCS): a method to accurately reconstruct dynamic CT images from highly under-sampled projection data sets Med. Phys. 35 660-3.

Depuydt T et al 2014 Treating patients with real-time tumor tracking using the Vero gimbaled linac system: implementation and first review Radiother. Oncol. 112 343-51.

Descovich M, Morin O, Aubry J F, Aubin M, Chen J, Bani-Hashemi A and Pouliot J 2008 Characteristics of megavoltage cone-beam digital tomosynthesis Med. Phys. 35 1310-16.

Furtado H, Steiner E, Stock M, Georg D and Birkfellner W 2013 Real-time 2D/3D registration using kV-MV image pairs for tumor motion tracking in image guided radiotherapy Acta. Oncol. 52 1464-71.

Gendrin C et al 2012 Monitoring tumor motion by real time 2D/3D registration during radiotherapy Radiother. Oncol. 102 274-80.

George R, Suh Y, Murphy M, Williamson J, Weiss E and Keall P 2008 On the accuracy of a moving average algorithm for target tracking during radiation therapy treatment delivery Med. Phys. 35 2356-65.

Godfrey D, Yin F, Oldham M, Yoo S and Willett C 2006 Digital tomosynthesis with an on-board kilovoltage imaging device Int. J. Radiat. Oncol. Biol. Phys. 65 8-15.

Guckenberger M, Meyer J, Wilbert J, Richter A, Baier K, Mueller G and Flentje M 2007 Intra-fractional uncertainties in cone-beam CT based image-guided radiotherapy (IGRT) of pulmonary tumors Radiother. Oncol. 83 57-64.

Hong J C et al 2013 Migration of implanted markers for image-guided lung tumor stereotactic ablative radiotherapy J. Appl. Clin. Med. Phys. 14 77-89 (PMID: 23470933).

Hugo G D, Liang J and Yan D 2010 Marker-free lung tumor trajectory estimation from a cone beam CT sinogram Phys. Med. Biol. 55 2637-50.

IEC 61217: Radiotherapy Equipment—Coordinates, Movements and Scales 2011 Technical Report International Electrotechnical Commission.

Imura M et al 2005 Insertion and fixation of fiducial markers for setup and tracking of lung tumors in radiotherapy Int. J. Radiat. Oncol. 63 1442-7.

James T D and Devon J G. Digital x-ray tomosynthesis: current state of the art and clinical potential. Phys Med Biol. 2003 September; 48(19) R65.

Johnson H J, McCormick M M and Ibanez L 2015 The ITK Software Guide Book 1: Introduction and Development Guidelines vol 1 (Clifton Park, N.Y.: Kitware).

Kavanagh A, Evans P M, Hansen V N and Webb S 2009 Obtaining breathing patterns from any sequential thoracic x-ray image set Phys. Med. Biol. 54 4879.

Keall P J et al 2006 The management of respiratory motion in radiation oncology report of AAPM Task Group 76 Med. Phys. 33 3874-900.

Kothary N, Heit J J, Louie J D, Kuo W T, Loo B W Jr, Koong A, Chang D T, Hovsepian D, Sze D Y and Hofmann L V 2009 Safety and efficacy of percutaneous fiducial marker implantation for image-guided radiation therapy J. Vasc. Interv. Radiol. 20 235-9.

Kupelian P et al 2007 Multi-institutional clinical experience with the Calypso System in localization and continuous, real-time monitoring of the prostate gland during external radiotherapy Int. J. Radiat. Oncol. 67 1088-98.

Lewis J H, Li R, Watkins W T, Lawson J D, Segars W P, Cervino L I, Song W Y and Jiang S B 2010 Markerless lung tumor tracking and trajectory reconstruction using rotational cone-beam projections: a feasibility study Phys. Med. Biol. 55 2505-22.

Maurer J, Godfrey D, Wang Z and Yin F F 2008 On-board four-dimensional digital tomosynthesis: first experimental results Med. Phys. 35 3574-83.

Poulsen P R, Cho B and Keall P J 2008 A method to estimate mean position, motion magnitude, motion correlation, and trajectory of a tumor from cone-beam CT projections for image-guided radiotherapy Int. J. Radiat. Oncol. 72 1587-96.

Poulsen P R, Fledelius W, Keall P J, Weiss E, Lu J, Brackbill E and Hugo G D 2011 A method for robust segmentation of arbitrarily shaped radiopaque structures in cone-beam CT projections Med. Phys. 38 2151-6.

Ren L, Zhang J, Thongphiew D, Godfrey D J, Wu Q J, Zhou S M and Yin F F 2008 A novel digital tomosynthesis (DTS) reconstruction method using a deformation field map Med. Phys. 35 3110-5.

Ren L, Zhang Y and Yin F F 2014 A limited-angle intrafraction verification (LIVE) system for radiation therapy Med. Phys. 41 020701.

Richter A, Wilbert J, Baier K, Flentje M and Guckenberger M 2010 Feasibility study for markerless tracking of lung tumors in stereotactic body radiotherapy Int. J. Radiat. Oncol. 78 618-27.

Rit S, Oliva M V, Brousmiche S, Labarbe R, Sarrut D and Sharp G C 2014 The Reconstruction Toolkit (RTK), an open-source cone-beam CT reconstruction toolkit based on the Insight Toolkit (ITK) J. Phys.: Conf. Ser. 489 012079.

Roman N O, Shepherd W, Mukhopadhyay N, Hugo G D and Weiss E 2012 Interfractional positional variability of fiducial markers and primary tumors in locally advanced non-small-cell lung cancer during audiovisual biofeedback radiotherapy Int. J. Radiat. Oncol. 83 1566-72.

Rottmann J, Keall P and Berbeco R 2013 Markerless EPID image guided dynamic multi-leaf collimator tracking for lung tumors Phys. Med. Biol. 58 4195-204.

Ruan D, Fessler J A, Balter J M and Keall P J 2009 Real-time profiling of respiratory motion: baseline drift, frequency variation and fundamental pattern change Phys. Med. Biol. 54 4777-92.

Santoro J et al. Evaluation of respiration-correlated digital tomosynthesis in lung. Med Phys. 2010 March; 37(3) 1237-45.

Seco J, Sharp G C, Wu Z, Gierga D, Buettner F and Paganetti H 2008 Dosimetric impact of motion in free-breathing and gated lung radiotherapy: a 4D Monte Carlo study of intrafraction and interfraction effects Med. Phys. 35 356-66.

Seiler P G, Blattmann H, Kirsch S, Muench R K and Schilling C 2000 A novel tracking technique for the continuous precise measurement of tumour positions in conformal radiotherapy Phys. Med. Biol. 45 N103.

Serpa M, Baier K, Cremers F, Guckenberger M and Meyer J 2014 Suitability of markerless EPID tracking for tumor position verification in gated radiotherapy Med. Phys. 41 031702.

Shah C, Grills I S, Kestin L L, McGrath S, Ye H, Martin S K and Yan D 2012 Intrafraction variation of mean tumor position during image-guided hypogractionated stereotactic body radiotherapy for lung cancer Int. J. Radiat. Oncol. 82 1636-41.

Sharp G C, Jiang S B, Shimizu S and Shirato H 2004 Tracking errors in a prototype real-time tumour tracking system Phys. Med. Biol. 49 5347.

Shieh C C, Kipritidis J, O'Brien R T, Cooper B J, Kuncic Z and Keall P J 2015 Improving thoracic four-dimensional cone-beam CT reconstruction with anatomical-adaptive image regularization (AAIR) Phys. Med. Biol. 60 841.

Sonke J J, Rossi M, Wolthaus J, van Herk M, Damen E and Belderbos J 2009 Frameless stereotactic body radiotherapy for lung cancer using four-dimensional cone beam CT guidance Int. J. Radiat. Oncol. 74 567-74.

Stevens C, Munden R, Forster K, Kelly J, Liao Z, Starkschall G, Tucker S and Komaki R 2001 Respiratory-driven lung tumor motion is independent of tumor size, tumor location, and pulmonary function Int. J. Radiat. Oncol. 51 62-8.

Tang X, Sharp G C and Jiang S B 2007 Fluoroscopic tracking of multiple implanted fiducial markers using multiple object tracking Phys. Med. Biol. 52 4081.

Teske H, Mercea P, Schwarz M, Nicolay N H, Sterzing F and Bendl R 2015 Real-time markerless lung tumor tracking in fluoroscopic video: handling overlapping of projected structures Med. Phys. 42 2540-9.

Trofimov A, Vrancic C, Chan T C Y, Sharp G C and Bortfeld T 2008 Tumor trailing strategy for intensity-modulated radiation therapy of moving targets Med. Phys. 35 1718-33.

van der Reijden A, van Herk M and Sonke J J 2013 Motion compensated digital tomosynthesis Radiother. Oncol. 109 398-403.

van der Voort van Zyp N C, Hoogeman M S, van de Water S, Levendag P C, van der Holt B, Heijmen B J and Nuyttens J J 2011 Stability of markers used for real-time tumor tracking after percutaneous intrapulmonary placement Int. J. Radiat. Oncol. 81 e75-81.

van Sornsen de Koste J R, Dahele M, Mostafavi H, Senan S, van der Weide L, Slotman B J and Verbakel W F A R 2013 Digital tomosynthesis (DTS) for verification of target position in early stage lung cancer patients Med. Phys. 40 091904.

van Sornsen de Koste J R, Dahele M, Mostafavi H, Sloutsky A, Senan S, Slotman B J and Verbakel W F A R 2015 Markerless tracking of small lung tumors for stereotactic radiotherapy Med. Phys. 42 1640-52.

Willoughby T et al 2006 Target localization and real-time tracking using the calypso 4D localization system in patients with localized prostate cancer Int. J. Radiat. Oncol. 65 528-34.

Yang Y, Zhong Z, Guo X, Wang J, Anderson J, Solberg T and Mao W 2012 A novel markerless technique to evaluate daily lung tumor motion based on conventional cone-beam CT projection data Int. J. Radiat. Oncol. 82 E749-56.

Zhang Y, Yin F F, Segars W P and Ren L 2013 A technique for estimating 4D-CBCT using prior knowledge and limited-angle projections Med. Phys. 40 121701.

BACKGROUND

Any discussion of the background art throughout the specification should in no way be considered as an admission that such art is widely known or forms part of common general knowledge in the field.

Almost all advances in cancer radiation therapy are driven by the twofold aim of maximising radiation dose to the tumor whilst minimising it elsewhere. By far the greatest impediment to this is the unpredictable location of the tumor during treatment, due to voluntary or involuntary patient motion (including respiration).

Often treatments further involve the added requirement for invasive procedures to implant markers or beacons to aid in tumor localisation. Currently, best-practice radiation therapy treatment involves pre-treatment imaging to ensure correct alignment of a patient relative to the planning images, and subsequent checks between or after treatment to ensure alignments are within a specified tolerance. Treatments often involve extra dose and larger margins to passively account for expected tumor motion.

A few treatment modalities involve monitoring of the tumor during treatment but these modalities are often invasive (requiring implantable markers or beacons), often very expensive and require large imaging doses to offset suboptimal image quality in a single X-Ray projection used to identify the target.

Lung tumors often exhibit large respiratory motion ranges (Barnes et al 2001, Stevens et al 2001, Keall et al 2006). The current standard of care of lung image-guided radiotherapy (IGRT) accounts for respiratory motion by adding margins to the target volumes based on the respiratory-correlated 4-dimensional (4D) planning CT, and delivering the dose with a static beam position based on a daily kV cone-beam CT (CBCT) scan. Consequently, changes in respiratory patterns and intrafraction deviations from mean CBCT tumor positions can degrade the delivered dose. Dosimetric differences on the order of 3-5% have been observed for large disparities in respiratory pattern between 4D CT and daily CBCT (Seco et al 2008). Intrafraction deviations in mean target position exceeding 5 mm have also been reported in >7% of treatments (Guckenberger et al 2007, Sonke et al 2009, Shah et al 2012). To ensure optimal radiation delivery, real-time guidance is desired.

Current real-time tumor tracking technologies rely on radiopaque fiducial markers (Seiler et al 2000, Sharp et al 2004, Tang et al 2007) or electromagnetic transponder beacons (Willoughby et al 2006, Kupelian et al 2007). However, marker or beacon implantation is an invasive, expensive, and time consuming procedure, and is not available at every radiotherapy clinic. Marker induced toxicity (Kothary et al 2009) and marker migrations (Imura et al 2005, van der Voort van Zyp et al 2011, Hong et al 2013) are also common problems. Markerless tumor tracking is thus desired.

Several markerless lung tumor tracking methods have been proposed using MV electronic portal imaging devices (EPID) (Richter et al 2010, Rottmann et al 2013, Bryant et al 2014, Serpa et al 2014) or kV imaging systems (Hugo et al 2010, Lewis et al 2010, Gendrin et al 2012, Yang et al 2012, van Sornsen de Koste et al 2015). MV EPID based methods are limited by the treatment field size and poor contrast. Richter et al (2010) reported that tumor visibility was insufficient for tracking in 53% of EPID images. On the other hand, kV imaging based methods benefit from a larger view and better image quality. Hugo et al (2010) have reported a mean tracking error of 2 mm using a 4D CT based template matching method on CBCT projection images. Also using a 4D CT template matching based method, Lewis et al (2010) have reported a maximum 95th percentile error of 3.3 mm Both methods were tested on phantom studies and two patient scans with relatively high tumor visibility, i.e. isolated or peripheral tumors. Gendrin et al (2012) proposed a fast GPU-based 2D/3D registration method that monitors both 2D translational motion and 3D rotational motion of the tumor with an update rate of 2 Hz. The method was further improved to include tracking along the kV beam direction by utilizing perpendicular MV EPID images (Furtado et al 2013). Phantom and patient cases were included in both studies, but no ground truth trajectory was available for evaluating tracking accuracies of the patient cases.

Existing markerless tracking methods rely on the tumors to be consistently visible on kV projection images (van Sornsen de Koste et al 2015). This raises challenges when the tumors are small, attached to nearby structures (e.g. central tumors), obstructed by high-density objects (e.g. bony anatomy), or when the radiological depth varies due to gantry rotation. In a study by Teske et al (2015), tumor visibility was insufficient for tracking in 6 out of 14 patients in the anterior-posterior (AP) view. More patients are expected to be ineligible for markerless tracking during gantry rotation. Yang et al (2012) used the average 4D CT image to subtract overlapping anatomies on the CBCT projection images by generating 'tumor-removed' digitally reconstructed radiographs (DRRs). The method was tested on one phantom and four patient scans, but no ground truth comparison was available for the patient cases. van Sornsen de Koste et al (2015) used a band-pass spatial filter to enhance tumor visibility on CBCT projections. The method was validated on five patients with a mean absolute tracking error of 0.5-1.4 mm. The fraction of kV images with insufficient tumor visibility for tracking was found to range from 2-64%. Several studies have exploited the potential of digital tomosynthesis (DTS) for 3D tumor localization (Godfrey et al 2006, Descovich et al 2008, Maurer et al 2008, Ren et al 2008, 2014, van der Reijden et al 2013, van Sornsen de Koste et al 2013, Zhang et al 2013).

SUMMARY OF THE INVENTION

It is an object of the invention, in its preferred form to provide an improved form of in situ targeting of objects.

In accordance with a first aspect of the present invention, there is provided a method for tracking a target located within a body, whilst scanning the body using X-ray projections, the method including the steps of: (a) providing a first prior image of the body and target indicating their relative position; (b) iteratively performing, for a series of time intervals, the steps of: (i) acquiring a few spatially distributed x-ray projections of the target area; (ii) determining one of a series of motion phases for each x-ray projection; (iii) performing an iterative reconstruction of the image for each of the motion phases; and (iv) outputting a resultant image for a current time interval.

The prior image can comprise an X-ray image of the target. The iterative reconstruction preferably utilises 4D cone beam CT to iteratively reconstruct the image. In some embodiments, the determining step utilises a motion sensor attached to the body to determine a current motion phase. In some embodiments, the time interval corresponds to that traversed by scanning equipment such as a linear accelerator gantry during about a 9 degree scanning arc.

In accordance with a further aspect of the present invention, there is provided a method of tracking a moving target within a body, the method including the steps of: (a) acquiring a first high resolution model of the target within the body; (b) forming a second high resolution model of the body without the target; (c) scanning the body in a series of segmented arcs, with the target having a series of phase positions within the arc; (d) forming a series of projection phase groupings for the scans; (e) determining a series of difference measures between the second high resolution model and the scanned series of projection phase groupings; and (f) utilising said difference measure to track an expected location of the target.

In some embodiments, the scanning comprises X-ray scanning of the body. The scanning can use the relative angular rotation between the patient and the imaging system. In some cases, about a 6 degree scanning arc is suitable. In some embodiments, the first high resolution model comprises a 4D CBCT model of the body. In some embodiments, the step (f) further comprises tracking the target using said difference measure and a series of constraints which localise movement of the target. The tracking can include optimising a minimization problem using conjugate gradient techniques. In some embodiments, the tracking includes forming a 3D centroid model of the target within the series of difference measures. The optimisation problem can include tracking the 3D centroid.

In accordance with a further aspect of the present invention, there is provided a method of tracking the 3D position of an in-situ target of a scanned imagery, the method including the steps of: (a) constructing a computational prior model of the target and its surrounding environment; (b) utilising one or more spatially distributed real-time 2D fluoroscopic image of the in-situ target to track the target; (c) comparing the computational prior model to the one or more spatially distributed 2D fluoroscopic image obtained in step (b); and (d) searching for a substantially optimal 3D target position, substantially minimizing the difference between the prior model and the fluoroscopic images.

In some embodiments, the in-situ target comprises a tumor and said computational prior model utilises a pre-treatment 4D cone-beam CT, and wherein said step (a) includes dividing the computational prior model into a model of the tumour and the surrounding anatomies based on a pre-treatment tumor contour formed around the tumor. In some embodiments, the method is applied to lung tumor tracking, and where the selection of multiple spatially distributed real-time 2D fluoroscopic images is performed based on a surrogate signal of respiratory motion. The step (c) can includes subtraction of the computational prior model from the 2D fluoroscopic images. The step (d) can include the minimisation of additional regularization terms that penalize large spatial deviations of the target from a prior position.

BRIEF DESCRIPTION OF THE DRAWINGS

Embodiments of the invention will now be described, by way of example only, with reference to the accompanying drawings in which.

DETAILED DESCRIPTION

The embodiments provide an advanced solution to identifying target motion inside the body using X-Rays across a large range of energies, including either kV or MV levels of energy. The embodiments of the invention have wide application in radiology, including interventional radiology, keyhole surgery and diagnostic imaging.

Embodiments of the invention provide for a non-invasive tracking of target motion that does not require implantation of markers. It can provide more robust, faster results which can result in a much reduced radiation dose to the patient being imaged. In addition, the embodiments are directed to the direct localization of the target radiation target rather than to the measurement of a surrogate (like a marker or landmarks in the body) and are therefore more robust and more accurate.

Alternative embodiments provide for a further simplification of the radiation therapy system removing the need for additional respiratory monitoring devices.

Figure 1:
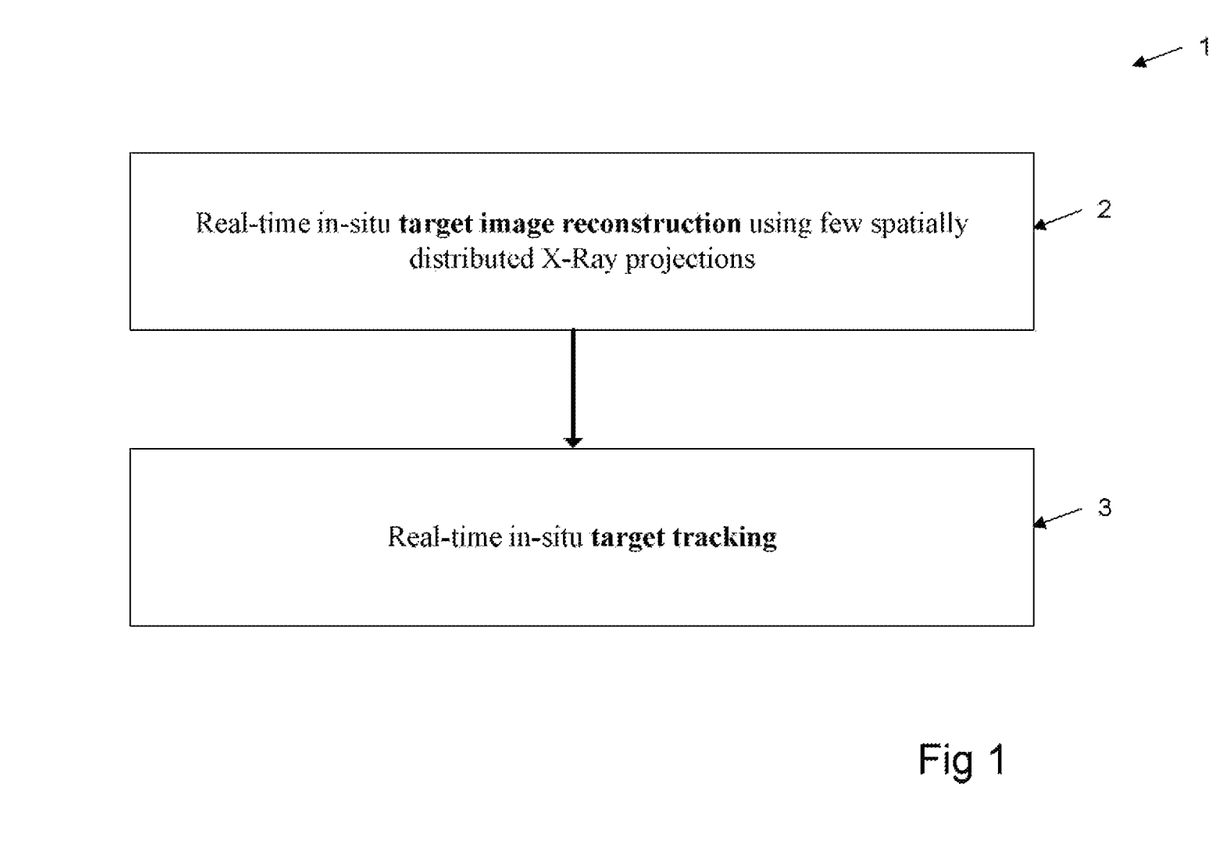
FIG. 1 illustrates a flow chart of the two step process of the preferred embodiment.

The embodiments utilise a reduced number of spatially distributed X-Ray projections for in-situ targeting of a moving objects within the body. Turning initially to FIG. 1, the steps 1 in the first embodiment include the two major components:

1. Real-time in-situ target image reconstruction using a few spatially distributed X-Ray projections The first component generates an image of the target with sufficient spatial information for localisation, whilst detecting the motion and deformation of the target from the image. The two components are described in the following sections.

Figure 2:
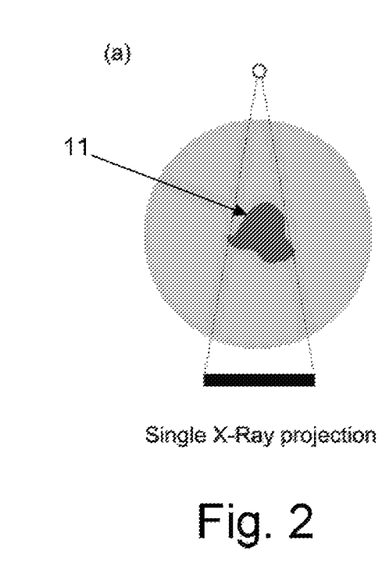
FIG. 2 illustrates schematically a single X-Ray projection.
Figure 3:
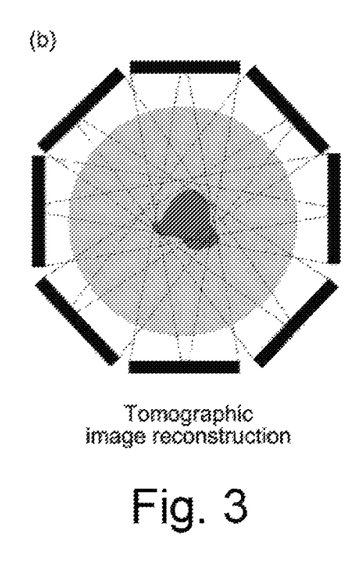
FIG. 3 illustrates schematically the process of tomographic image reconstruction (which normally requires a full set of spatially distributed X-Ray projections spanning 360 degrees)

1. Real-Time In-Situ Target Image Reconstruction Using a Few Spatially Distributed X-Ray Projections In-situ target localisation using a single X-Ray projection as shown in FIG. 2 is rarely achievable due to the inferior image contrast caused by nearby objects that overlap with the target 11 along the X-Ray. On the other hand, tomographic image reconstruction that utilizes a full set of spatially distributed X-Ray projections spanning at least 180 degrees, as shown schematically in FIG. 3, provides high quality three-dimensional (3D) image of the target, but often requires prolonged scan time and does not render real-time information of the target.

Figure 4:
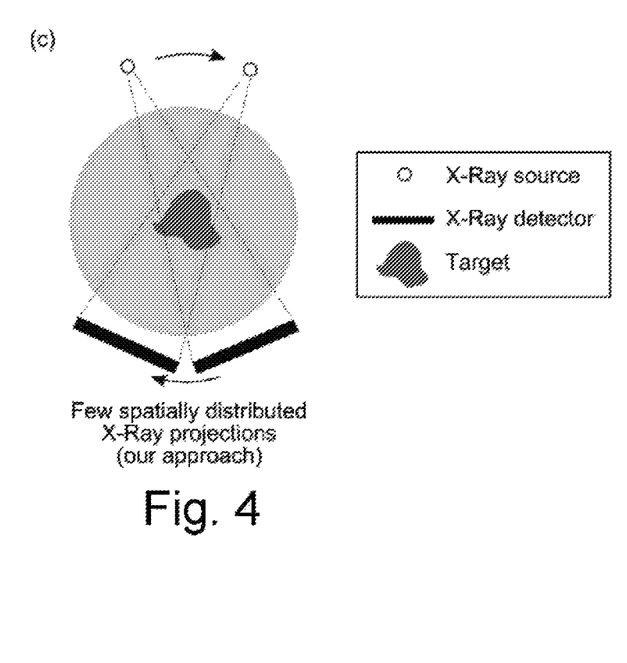
FIG. 4 illustrates schematically the process of utilising a few spatially distributed x-ray projections for target image reconstruction.

In the first embodiment, a few spatially distributed X-Ray projections, as illustrated schematically in FIG. 4, are acquired within a short time interval (20 seconds or less) for real-time 3D in-situ target tracking. By using more than one X-Ray projection, the additional spatial information allows the target to be delineated from the surrounding objects. Furthermore, the much shorter scan time compared to tomographic image reconstruction enables real-time localisation of the target.

The In-situ target image reconstruction using only a few spatially distributed X-Ray projections is challenging because the small amount of acquired data is often insufficient to determine the 3D structure and location of the target. However, this can be overcome by incorporating the following into the image reconstruction procedure of FIG. 5 which includes:

A. A High-Quality Prior Image of the Target 51

Figure 5:
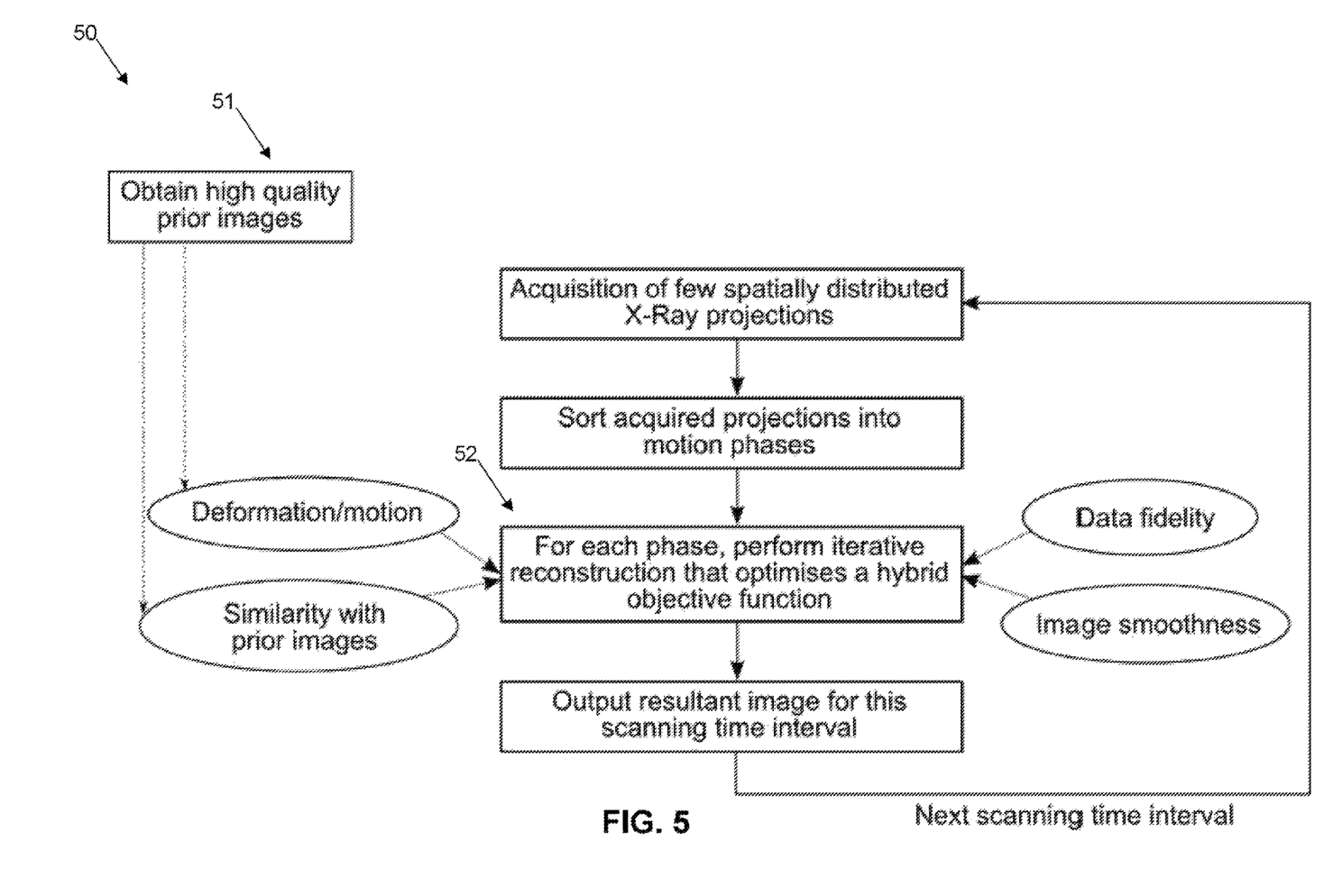
FIG. 5 illustrates a flow chart outlining the in-situ target image reconstruction using few spatially distributed X-Ray projections.

A prior image is a pre-acquired 4D-CBCT image of the target and its neighbouring region. A high-quality prior image is significant as it provides knowledge of how the target can be differentiated from surrounding objects.

In radiotherapy, a set of tomographic images of the patient are usually acquired immediately before treatment for patient setup, and are suitable prior images because they very closely represent the patient anatomy during the treatment.

Whilst different methodologies can be utilised to acquire the prior image, the one embodiment utilised the technique disclosed in Shieh C C et al. 2015 to provide a high level of image quality of the prior image.

B. An Iterative Image Reconstruction Algorithm 52

Image reconstruction techniques that utilise a limited spatial span of X-Ray projections exist in radiotherapy, and are referred to as digital tomosynthesis (DTS) (James T D and Devon J G 2003). DTS is mostly used for patient setup imaging and employs X-Ray projections of significant span. In the first embodiment, a much smaller angular range (~10 degrees) is required in order for a time resolution sufficient for real-time target localisation. For this purpose, an iterative DTS reconstruction algorithm was developed to address the following challenges:

a. The small angular range of X-Ray projections result in the lack of information of the target structure and position along the X-Ray direction. This can be overcome by imposing a similarity constraint between the high-quality prior image and the resultant, in which case full 3D information of the prior image can be incorporated.

b. The target is likely to exhibit motion even within the short scanning interval. In lung cancer radiotherapy, the motion is mainly caused by respiration, and can be estimated by an external surrogate, e.g. infrared signals that measure the patient abdominal motion. The few X-Ray projections can then be sorted into several respiratory phases and reconstructed into separate images, within each of which the motion is minimal (Santoro J et al. 2010).

c. Intrinsic noise in the X-Ray projections has severe impact on the image quality when only few X-Ray projections are used. This can be overcome by adding a regularization constraint in the iterative process to reduce noise and artefacts.

d. The target is likely to have different structures (deformation) and positions (translational motion) in the prior image and during the scan. Such disparities can be jointly estimated together with the resultant image by adding constraints on the degree of deformation and motion in the iterative process. Similar techniques are provided in Ren L et al 2008.

e. The confidence level of the knowledge about the tumor can be dynamic and dependent on the angles and number of projections used in a specific image reconstruction. To account for this, all the constraints described above can be adaptively adjusted based on some measure of confidence.

In summary, the target image reconstruction algorithm can be a hybrid DTS approach that combines several techniques to overcome challenges incurred from the use of limited spatial span of X-Ray projection data. The iterative reconstruction procedure is in the form of an optimisation problem where the objective function to be optimised is an adaptive combination of data fidelity, image smoothness, and deformation/motion/similarity between the prior and resultant image.

FIG. 5 illustrates the flow chart that outlines the above procedural steps.

Figure 6:
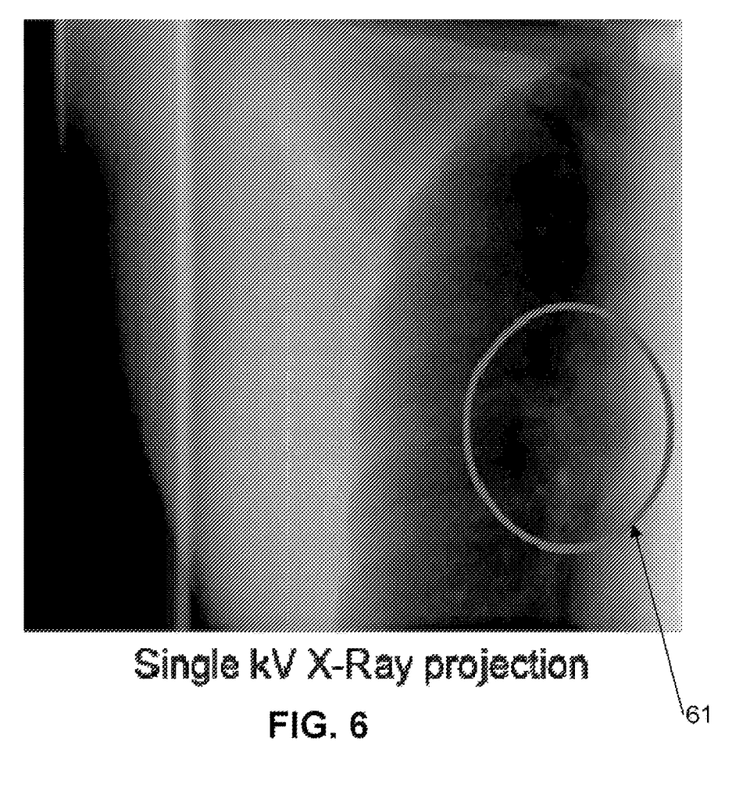
FIG. 6 illustrates an image of a lung cancer radiotherapy patient obtained from a single kV X-Ray projection.
Figure 7:
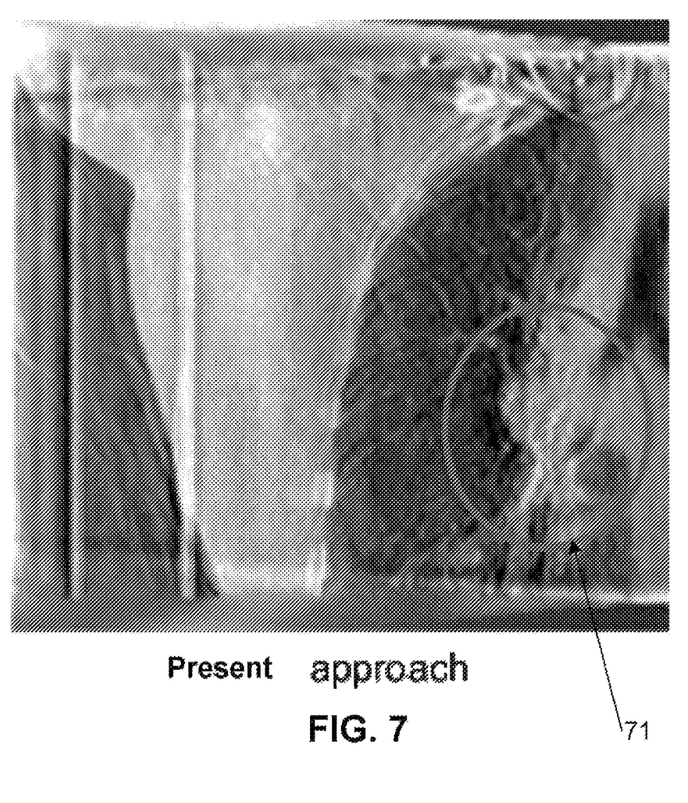
FIG. 7 illustrates an image of a lung cancer radiotherapy patient obtained from in-situ target image reconstruction using few spatially distributed X-Ray projections.

The procedural steps were tested on a lung cancer radiotherapy patient. FIG. 6 shows the image obtained from a single kilo-voltage (kV) X-Ray projection, with FIG. 7 showing a resultant image using the above technique. The method of the preferred embodiment has significantly improved the contrast and definition of the target, i.e. the tumor highlighted by circles 61, 71, enabling delineation of the target from the surrounding objects and in-situ localisation.

Figure 8:
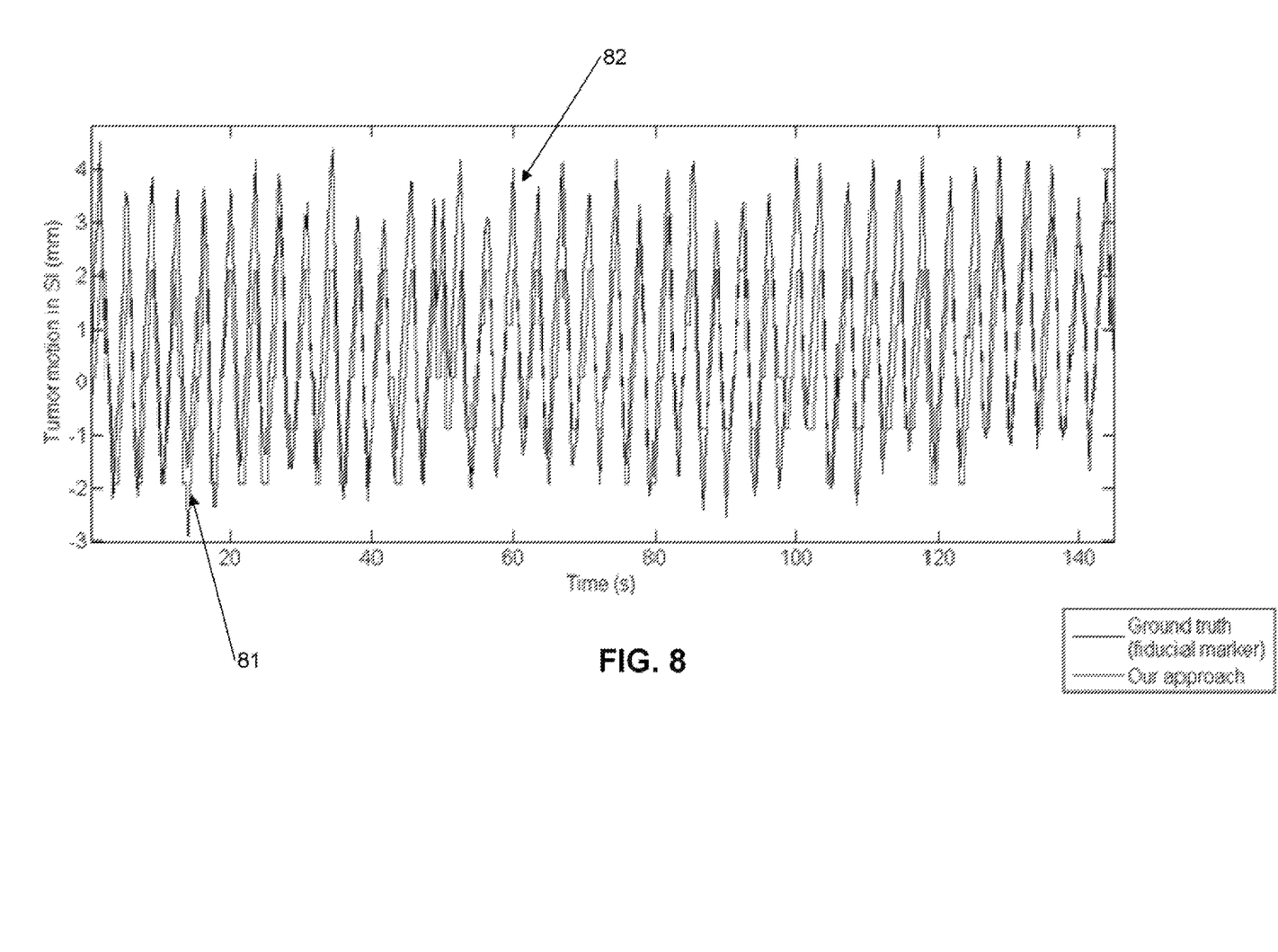
FIG. 8 illustrates an example of the tumor tracking of the preferred embodiment compared with fiducial marking tracking.

To demonstrate the feasibility of real-time localisation using our invention, FIG. 8 displays the trajectory of the tumor in the superior-inferior (SI) direction obtained using our approach during a two minute imaging session. A radiopaque fiducial marker was previously implanted in the tumor, the trajectory of which can be accurately measured (shown in black) and used as a ground truth. The approach of the preferred embodiment was able to localise the tumor within an accuracy of approximately 2 mm. The rapid oscillating respiratory motion pattern and the long term motion trend were both well captured.

Alternative Embodiment

Figure 9:
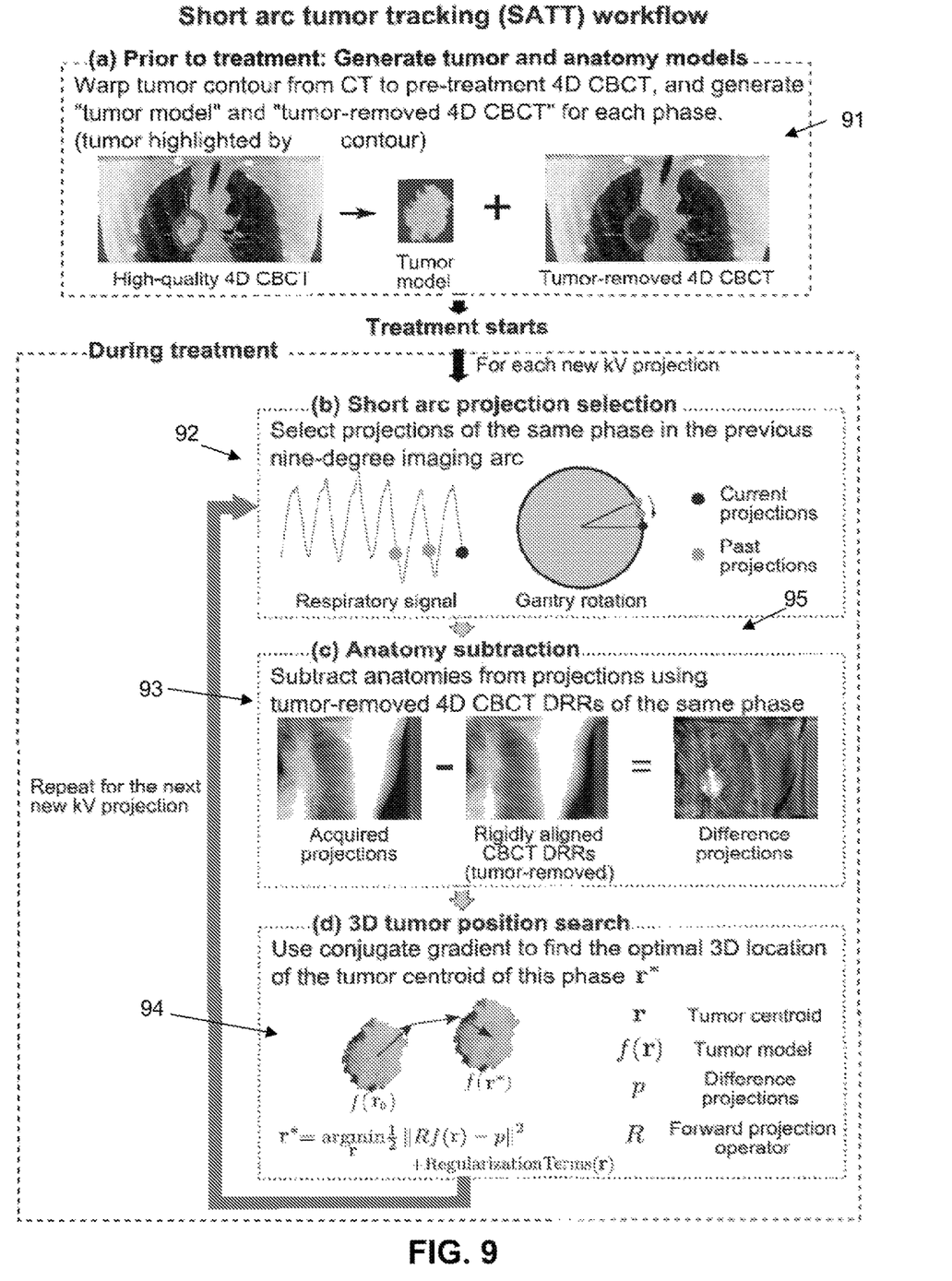
FIG. 9 illustrates the flow of an alternative embodiment of the invention.

An alternative embodiment of the present invention will now be described with reference primarily to FIG. 9 which discloses the steps in a more direct tumor localisation method.

In this method, the target tumor is tracked again with significant undersampling of the tumor body. This allows for real time tracking of tumors during relative movement of the scanning system and human body. The limited number of projections allows for tracking in the absence of tomosynthesis. This embodiment aggressively utilises the prior knowledge contained in the image prior.

In this embodiment, an initial prior image is provided by means of 4D CBCT. Techniques such as those disclosed in Shieh C C 2015 can be utilised to provide the 4D prior image which includes breathing phase information. The 4D CBCT imagery can be acquired by many different means. For example by CT imagery.

Ideally, a high quality 4D CBCT (AAIR) image is used for removing anatomies—a standard FDK 4D CBCT reconstructions may not provide signal significance which wouldn't be able to generate DRRs that help remove the anatomies very well.

The first step 91 is to forward project the 4D CBCT imagery into the 2 dimensional domain for each angle and breathing phase and to segment and extract out the tumor from the imagery to produce a non tumor 4D CBCT image, which highlights a background non tumor modelling.

Next, 92, for a current imaging arc, which in some embodiments can be around 9 degrees, the projections are sorted into breathing phases.

Next 93, the anatomy structure is subtracted from the acquired projections using the non-tumor 4D CBCT images to determine a difference projection, which highlights the tumor structure.

Next, an optimisation process, such as the conjugate gradient method, is utilised to find the optimal 3D location of the tumor model for this phase.

So the reconstruction problem becomes a minimisation of:

$$(x,y,z)^* = \mathrm{argmin} |Rf(x,y,z)-p|^2 + \mathrm{OtherConstraints}(x,y,z) \quad \text{(Eqn 1)}$$

Where R is the forward projection operator, f(x,y,z) is the tumor model form the 4D CBCT as a function of its centroid x,y,z. p is the difference projection with is the actual treatment projection.

The argmin portion of equation 1 comprises the difference projection. Other constraints can include restrictions on tumor movement. For example, that the tumor can only move minimally in the direction along the DTS angle (where resolution is poorest) compared to the previous frame, only to stabilize the tracking.

Expressing the problem in this manner has the advantages that the objective function is convex, differentiable, and its gradient & Hessian can be calculated easily using finite difference and forward projection. This means the function is amenable to conjugate gradient solution techniques.

The minimum can be taken as the most likely tumor centroid position. The tumor modelling acts to significantly reduce the number of variables to be solved.

This embodiment makes a number of assumptions to reduce complexity. These assumptions include: 1. Anatomies except for the tumor do not change significantly between pre-treatment and treatment session (of the same respiratory phase). This assumption is applied by subtracting the rigidly aligned DRR generated from the anatomy-only (tumor removed) 4D CBCT of the same phase from the treatment projection. 2. Tumor positions are similar within the same phase and within a 9-degree imaging arc. This assumption is applied by respiratory sorting and using multiple projections. 3. The shape of the tumor does not change between pre-treatment 4D CBCT and treatment (of the same phase). This assumption is applied by using the tumor model extracted from 4D CBCT and only allowing it to move rigidly in x,y,z for matching the projections. In other words, instead of solving all pixel values in our 3D image, it is only necessary to solve for three variables—x, y, z, the tumor centroid coordinate. (Deformation can also be included if we can express the image as a function of several important deformation parameters, like size).

This embodiment also allows for the use of multiple projections, which ensures we have enough information to determine x,y,z, location and also that the matching would be less prone to noise/artifacts/overlapping anatomies in a particular projection.

Further Alternative Embodiment

In the embodiments of the invention, a 3D markerless lung tumor tracking method and apparatus is provided based on kV imaging under gantry rotation that is robust to inferior tumor visibility. One method, referred as the short arc tumor tracking (SATT) method, differs from other markerless tracking approaches in that a nine-degree imaging arc is utilised and incorporate respiratory-correlated 4D CBCT prior knowledge.

Short Arc Tumor Tracking (SATT):

The workflow of the SATT method is as outlined previously in FIG. 9, with a number of refinements discussed hereinafter.

Initially, the tumor has been contoured on the planning CT, and a respiratory-correlated 4D CBCT scan prior to the treatment is provided available. The method can utilise the Insight Toolkit (ITK) (Johnson et al 2015) and Reconstruction Toolkit (RTK) (Rit et al 2014).

The four major steps are described in detail in the following sections.

Generate Tumor and Anatomy Models, 91.

Prior to the treatment, 4D models of the tumor and the surrounding anatomy are generated from pre-treatment 4D CBCT images. This is done by warping the tumor contour on the planning CT onto the 4D CBCT using deformable image registration (DIR). For each phase of the 4D CBCT, a tumor model and a 'tumor-removed' 4D CBCT image are generated (91). The former is a direct extraction of the 4D CBCT image pixels within the warped contour, while the latter is the 4D CBCT image with pixel values within the warped contour set to zero attenuation. The tumor models represent the targets to be tracked, and the tumor-removed 4D CBCT images are anatomy models that estimate the contribution of surrounding anatomies to the integral attenuation on kV projection images. The qualities of both models are dependent on the quality of the 4D CBCT images. In one example, the 4D CBCT images were reconstructed using a previously developed anatomical-adaptive image regularization (AAIR) technique to reduce noise and streaking artifacts while preserving image sharpness (Shieh et al 2015), combined with the prior-image-constrained-compressed-sensing (PICCS) algorithm (Chen et al 2008) to improve the contrast of the bony anatomy. Other techniques can be used to reduce noise.

Short Imaging Arc Projection Selection (92).

During the treatment, tracking is performed at every kV projection acquisition time stamp. For each new kV projection, the respiratory phase is first determined by the projection intensity analysis method (Kavanagh et al 2009). In this work, retrospective respiratory phase was used. In practice, real-time phase can be calculated using the method proposed by Ruan et al (2009). Projections of the same phase in the previous nine-degree imaging arc are then selected (92). The arc size of nine degrees was chosen as it was found to be the smallest arc that rendered successful tracking. Compared to using a single projection, a nine-degree arc exploits the 3D information of the tumor in multiple views, making it possible to track cases that would otherwise be challenging, e.g. tumors attached to neighboring structures. In addition, a nine-degree imaging arc can be acquired within 1.5-9s with a typical gantry speed of 1-6 deg s$^{-1}$, which is in general a sufficiently short time interval for the time resolution required for treatment guidance. A larger arc of thirty degrees was tested and found to slightly improve tumor localization, but at the same time further degrade the time resolution, leading to overall similar tracking performance. In practice, the optimal arc size may depend on multiple factors such as the visibility, size, and location of the tumor, and gantry speed.

Anatomy Subtraction (93).

Before the projections selected in the previous step are used for tumor position matching, the contribution of all the anatomies except for the tumor to the integral attenuation values is first estimated and subtracted from the projections. This is done by first forward projecting the tumor-removed 4D CBCT image of the same phase to generate tumor-removed DRRs at the gantry angles of the selected projections. Each DRR is then rigidly registered to and subtracted from the corresponding projection, resulting in a set of 'difference projections' (95). The difference projections, denoted as p, are assumed to contain only attenuation contributed from the tumor, therefore the exact tumor position can be found by matching the tumor model with p. In practice, however, exact subtraction of anatomies from the projections is not possible due to the change in patient anatomy during treatment and the approximation errors from the reconstructed 4D CBCT images and DRRs.

3D Tumor Position Search (94).

The tumor position can be found by rigidly moving the tumor model f in the 3D space until the optimal match between the forward projections of the tumor model Rf and the difference projections p is reached, where R is the forward projection operator. Assuming no rotation and deformation of the tumor within the same respiratory phase, the tumor model can be considered a function of its centroid position f (r), where r=[x, y, z]$^T$ (in mm) is the tumor centroid expressed in the IEC 61217 geometry standard, i.e. x is left-right (LR), y is superior-inferior (SI), and z is anterior-posterior (AP) (IEC 61217: Radiotherapy Equipment—Coordinates, Movements and Scales 2011). The problem of searching for the optimal tumor centroid position r* can then be described as the following optimization problem:

$$r^* = \mathrm{argmin}_r \frac{1}{2}\|Rf(r) - p\|^2 + \lambda_{ID}[(\hat{u}_{ID})^T(r - r_{Prior})]^{2\gamma_{ID}} + \qquad (1)$$

$$\lambda_{Lat}[(\hat{u}_{Lat})^T(r - r_{Prior})]^{2\gamma_{Lat}} + \lambda_{SI}[(\hat{u}_{SI})^T(r - r_{Prior})]^{2\gamma_{SI}},$$

$$\lambda_{ID}, \lambda_{Lat}, \lambda_{SI} \geq 0.$$

$$\gamma_{ID}, \gamma_{Lat}, \gamma_{SI} \geq 1.$$

The first term of the objective function represents the L2-norm of the disparity between Rf (r) and p. The other three terms are regularization terms that prevent erroneous tracking results which can potentially be caused by inferior anatomy subtraction. For example, residual highly attenuated structures in the difference projections. The regularization terms penalize tracking results that deviate considerably from an a priori tumor position $r_{Prior}$ based on the squared distances in the kV short arc in-depth (ID), lateral (Lat), and SI directions, respectively. The in-depth directional vector $\hat{u}_{ID}=[-\sin\bar{\theta}, 0, \cos\bar{\theta}]^T$ is defined to be in the direction of the middle angular value $\bar{\theta}$, of the selected projections, while the lateral directional vector $\hat{u}_{LAT}=[-\sin\bar{\theta}, 0, \cos\bar{\theta}]^T$ is defined to be perpendicular to both $\hat{u}_{ID}$ and the SI directional vector $\hat{u}_{SI}=[0, 1, 0]^T$. The γ's are introduced as parameters to adjust the powers of the squared distances, as higher power terms are more forgiving to small deviations while more intolerant to large deviations. In other words, with larger γ values, the regularization terms have smaller effects on the tracking results when r is reasonably close to $r_{Prior}$, and larger effects when r deviates significantly from $r_{Prior}$. In this example, all the γ's were set to 2. The λ's control the regularization strengths in the in-depth, lateral, and SI directions. In general, $\lambda_{ID}$ is larger than $\lambda_{Lat}$ and $\lambda_{SI}$ as the selected projections contain much less information in the in-depth direction than in the lateral and SI directions. In this work the $\lambda$ values were selected based on a heuristic scheme such that the regularization terms have minimal influences on tracking when $\|r-r_{Prior}\|$ is small, and start to have noticeable impacts only when $\|r-r_{Prior}\|$ is larger than a certain threshold.

The local minima of (1) can be solved by the nonlinear conjugate gradient method. The objective function in (1) is generally not convex and has multiple minima, because the anatomy subtraction is often imperfect and can cause residual highly attenuated structures in p that may mislead the tracking. Nevertheless, with appropriate regularization and initialization of r, the algorithm can mostly be guided towards the minimum of interest, i.e. the solution that closely represents the true tumor centroid. The nonlinear conjugate gradient method often converges to the closest minimum, and tumors generally have minimal motion between consecutive kV projection acquisitions provided the typical acquisition rate is about 5 Hz. Thus, in this work the initial $r_0$ was set to the tumor centroid position tracked in the previous kV acquisition time stamp. In addition, the tumor centroid position in the 4D CBCT image of the same phase was used as $r_{Prior}$ for regularization to stabilize the tracking.

Results

The system of the embodiment was retrospectively validated SATT on kV imaging datasets from an NCI-sponsored lung cancer trial with seven locally advanced non-small-cell lung cancer patients treated with definitive radio-chemotherapy with 3D conformal radiotherapy (see Roman et al (2012) for detailed descriptions of the datasets). These patient cases represent challenging scenarios for markerless tumor tracking, as the tumors were attached to the mediastinum and cannot be visually identified in most of the kV projection images due to inferior adjacent contrast. Each patient was implanted with 2-4 fiducial gold coil markers within and/or around the tumor, the trajectory of which was used in this work as the ground truth for computing tracking accuracy. The system was found to provided markerless lung tumour tracking.

The SATT methodology provides a markerless lung tumor tracking method that employs extremely short imaging arc projection matching (nine degrees) and 4D CBCT prior knowledge. These two components enable tumors with inferior visibility on the kV projection images to be directly tracked.

SATT utilises a pre-treatment 4D CBCT scan and continuous kV image acquisition during treatment delivery, which are both readily compatible with the workflow of modern radio-therapy. The tumor tracking procedure does not interfere with the treatment procedures as it is performed independently of treatment delivery. The short-arc nature of SATT assumes delivery techniques that involve continuous gantry rotation, e.g. Volumetric Modulated Arc Therapy. Nevertheless, the methodology of SATT can also be applied to treatments with static gantry such as step-and-shoot Intensity-Modulated Radiation Therapy and conformal radio-therapy. In these treatment scenarios, the short arc selection step reduces to using one single projection. In addition, stronger in-depth regularization (higher 6) is needed to compensate for the loss in in-depth resolution.

In trials, trajectory errors were significantly smaller with tracking as compared to CBCT for all scans, and the improvements were most significant for tumors with large deviations from the mean CBCT locations. This highlights the usefulness of SATT in IGRT, as it always provides more accurate position information than the standard of care, and especially when large tumor excursions are present.

Tracking accuracy was found to vary from case to case. Larger trajectory errors were observed for cases with large deviations from the mean CBCT locations. This is most likely because large tumor excursions often accompany changes in surrounding anatomies especially for tumors attached to nearby structures, thereby degrading the accuracy of the 4D CBCT anatomy models. Nevertheless, the use of 4D CBCT prior knowledge is still expected to be more accurate than methods based on 4D CT prior models (Hugo et al 2010, Lewis et al 2010). The improvements relative to CBCT were found to be larger in the SI direction and smaller in the MV lateral direction. This is because tracking in the MV lateral direction, which is almost parallel to the kV short arc in-depth direction, is ill-posed, thus increasing the impacts of the 4D CBCT based regularization terms. Tracking in the MV lateral direction is a common challenge to kV imaging based approaches on most commercial linacs with perpendicular kV-MV orientation. Techniques that utilize both kV and MV images can be used to improve MV lateral tracking accuracies (Furtado et al 2013, Ren et al 2014). Alternatively, better MV lateral tracking accuracies may exist if SATT is implemented on linacs with non-perpendicular kV-MV orientation, such as the Vero SBRT system (BrainLab AG, Feldkirchen, Germany) (Depuydt et al 2014).

Comparisons with Other Studies:

Several kV imaging based markerless tracking methods have been proposed and tested on clinical cases. Hugo et al (2010) reported a mean tracking error of 2 mm Lewis et al (2010) reported a maximum 95th percentile error of 3.3 mm van Sornsen de Koste et al (2015) found the mean tracking error on the projection domain to be 0.5-1.1 mm. These studies investigated mainly isolated tumors, which have relatively high visibility on kV projection images. The results are similar to that observed in this work for the good case scenarios. In addition, the results reported by Hugo et al (2010) and Lewis et al (2010) were obtained for only two clinical scans. van Sornsen de Koste et al (2015) investigated a total of 22 scans, and found that the fraction of kV images with insufficient tumor visibility for tracking ranges from 2-64%. Teske et al (2015) also reported in their study that tumor visibility was insufficient for tracking in 6 out of 14 patients in the AP view. In contrast, methods of these embodiments were able to track the tumors at gantry angles regardless of the inferior tumor visibility. Compared to single projection based template matching methods, this method allows more patients to be eligible for and benefit from markerless guidance.

The SATT method provides a markerless lung tumor tracking method based on short kV imaging arcs and 4D CBCT prior knowledge, to address the challenge of inferior tumor visibility in markerless tracking. The embodiments work well on patients with central tumors, which are difficult to track due to the lack of adjacent contrast.

The SATT is robust to low tumor visibility, and can potentially allow more patients to be eligible for markerless real-time guidance. The tumor localization accuracies are also significantly improved.

Interpretation

Reference throughout this specification to "one embodiment", "some embodiments" or "an embodiment" means that a particular feature, structure or characteristic described in connection with the embodiment is included in at least one embodiment of the present invention. Thus, appearances of the phrases "in one embodiment", "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms comprising, comprised of or which comprises is an open term that means including at least the elements/features that follow, but not excluding others. Thus, the term comprising, when used in the claims, should not be interpreted as being limitative to the means or elements or steps listed thereafter. For example, the scope of the expression a device comprising A and B should not be limited to devices consisting only of elements A and B. Any one of the terms including or which includes or that includes as used herein is also an open term that also means including at least the elements/features that follow the term, but not excluding others. Thus, including is synonymous with and means comprising.

As used herein, the term "exemplary" is used in the sense of providing examples, as opposed to indicating quality. That is, an "exemplary embodiment" is an embodiment provided as an example, as opposed to necessarily being an embodiment of exemplary quality.

It should be appreciated that in the above description of exemplary embodiments of the invention, various features of the invention are sometimes grouped together in a single embodiment, FIG., or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical or electrical contact, or that two or more elements are not in direct contact with each other but yet still co-operate or interact with each other.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

The invention claimed is:

1. A method of predicting a 3D target position of a moving in-situ target in a body, the method comprising:
   (a) providing a computational prior model of a moving in-situ target in a body and the surrounding environment of the moving in-situ target;
   (b) selecting a respiratory phase of the computational prior model using a surrogate signal of respiratory motion to provide a computational prior model of the moving in-situ target and the surrounding environment of the moving in-situ target at a selected respiratory phase;
   (c) dividing the computational prior model of the moving in-situ target and the surrounding environment of the moving in-situ target at the selected respiratory phase to provide: 1) a target model of the moving in-situ target; and 2) an anatomy-only model of anatomies surrounding the moving in-situ target, wherein said anatomy-only model does not provide a model of said moving in-situ target;
   (d) selecting one or more spatially distributed real-time 2D image of the moving in-situ target at the selected respiratory phase using the surrogate signal of respiratory motion;
   (e) comparing the anatomy-only model to the one or more spatially distributed real-time 2D image; and
   (f) minimizing a difference between the anatomy-only model and the one or more spatially distributed real-time 2D image to predict the 3D target position of the moving in-situ target in a body.

2. The method as claimed in claim 1, wherein the moving in-situ target comprises a tumor and dividing the computational prior model provides a model of the tumor and an anatomy-only model of anatomies surrounding the tumor based on a pre-treatment tumor contour formed around the tumor.

3. The method as claimed in claim 1, wherein said method is applied to tumor tracking, and wherein comparing the anatomy-only model to the one or more spatially distributed real-time 2D image comprises subtracting the anatomy-only model from the one or more spatially distributed real-time 2D image.

4. The method as claimed in claim 1, wherein said method is applied to tumor tracking, and comparing the anatomy-only model to the one or more spatially distributed real-time 2D image comprises minimizing additional regularization terms that penalize large spatial deviations of the moving in-situ target from a prior position.

5. The method as claimed in claim 4, wherein the prior position is the moving in-situ target position measured in the computational prior model.

6. The method as claimed in claim 1, wherein said computational prior model comprises a pre-treatment 4D cone-beam CT image.

7. A method of predicting a 3D position of a moving in-situ tumor in a body, the method comprising:

(a) providing a computational prior model of a moving in-situ tumor in a body and anatomies surrounding the moving in-situ tumor;

(b) selecting a respiratory phase of the computational prior model using a surrogate signal of respiratory motion to provide a computational prior model at the selected respiratory phase of the moving in-situ tumor and anatomies surrounding the moving in-situ tumor;

(c) removing said moving in-situ tumor from said computational prior model at the selected respiratory phase to provide an anatomy-only model;

(d) selecting one or more spatially distributed real-time 2D image of the moving in-situ tumor at the selected respiratory phase;

(e) comparing the anatomy-only model to the one or more spatially distributed real-time 2D image; and (f) minimizing a difference between the anatomy-only model and the one or more spatially distributed real-time 2D image to predict the 3D position of the moving in-situ tumor in a body.

* * * * *